United States Patent [19]

Garabedian

[11] Patent Number: Plant 7,076

[45] Date of Patent: Dec. 19, 1989

[54] PLUM TREE, GAR-RED

[76] Inventor: John M. Garabedian, P.O. Box 7883, Fresno, Calif. 93747

[21] Appl. No.: 268,346

[22] Filed: Nov. 7, 1988

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of Plum Tree, denominated varietally as "Gar-Red" and which is characterized as to novelty by a date of maturity for commercial harvesting and shipment of approximately August 10 through August 15 under the ecological conditions prevailing in Fresno, Calif., in the central part of the San Joaquin Valley of central California.

1 Drawing Sheet

BACKGROUND OF THE NEW VARIETY

The present invention relates to a new and novel variety of Plum Tree, hereinafter denominated varietally as "Gar-Red" and more particularly to such a plum tree which produces semi-freestone fruit having a pleasing shape and which further are ripe for commercial harvesting and shipment approximately August 10 through August 15 under the ecological conditions prevailing in Fresno County, Calif. The new variety of Plum Tree appears to produce fruit which have somewhat similar characteristics as compared with the Gar Fantasy Plum Tree, (U.S. Plant Pat. No. 5,178), but is distinguishable therefrom and characterized principally as to novelty by being ripe for harvesting the shipment approximately five or six weeks before the Gar Fantasy Plum Tree at the same Fresno County location.

The inventor has during his professional career, produced scores of new varieties of fruit trees, as well as developed a multiplicity of new and novel grapevines. During the course of the several decades when the applicant developed these new and novel varieties of plants, he routinely studied and evaluated chance open-pollinated fruit trees of unknown parentage in an effort to ascertain whether any new and distinct varieties were evident. The present variety of Plum Tree "Gar-Red" is a product of the above-identified procedure.

ORIGIN AND ASEXUAL REPRODUCTION OF THE NEW VARIETY

The present variety of Plum Tree Gar-Red is believed to be an open-pollinated chance seedling of unknown parentage, which was discovered by the inventor in 1982, within the cultivated area of his test block of trees which were then growing on his Ranch No. 1 which is located on the corner of Fowler and Kings Canyon Avenues, in Fresno, Fresno County, Calif. The inventor observed that the open-pollinated chance seedling produced fruit which had noteworthy characteristics, and in accordance with his standard practice, he marked the seedling for future observation. In an effort to determine whether the new variety of plum tree had stable characteristics, the applicant asexually reproduced the new variety, in 1983, by removing bud wood from the open-pollinated seedling and by budding it into mature plum trees and plum rootstock, which were then growing on applicant's Ranch No. 3 which is located along Belmont Avenue, in Fresno, Fresno County, Calif. These budded test trees and plum rootstock have been continually observed by the inventor and it has subsequently been determined that the progeny produced by these test trees and plum rootstock possess the same distinctive characteristics as that originally observed in the original open-pollinated plum tree.

SUMMARY OF THE NEW VARIETY

The Gar-Red Plum Tree is characterized principally as to novelty by producing a good quality mid-season plum. The present variety of plum tree bears fruit which appear most closely similar in their external appearance to the fruit produced by the Gar Fantasy Plum Tree (U.S. Plant Pat. No. 5,178), but is distinguishable therefrom by bearing semi-freestone fruit which are ripe for harvesting and shipment on August 10 through August 15 under the ecological conditions prevailing in Fresno County, Calif.

BRIEF DESCRIPTION OF THE DRAWINGS

The accompanying drawing is a color photograph of a characteristic twig bearing typical leaves, several mature fruit showing their external coloration sufficiently mature for harvesting and shipment, two fruit of the subject variety dissected in the axial plane to illustrate the flesh characteristics thereof, and several stones, all of the subject variety.

DETAILED DESCRIPTION

Referring more specifically to the pomologocal details of this new and distinct variety of Plum Tree, the following has been observed under the ecological conditions prevailing at the orchard of the inventor which is located in Fresno, Calif. All major color code designations are by reference to the Dictionary of Color by Maerz and Paul, Second Edition, 1950. Common color names are also employed occasionally.

TREE

Generally:

*Size.*—Medium to large as compared with other common plum cultivars growing in the San Joaquin Valley of central California.

*Vigor.*—Average and tender.

*Form.*—Upright, dense and vase formed, depending upon pruning practices.

*Productivity.*—Variable, the variety is generally considered mediumly productive.

*Regularity of bearing.*—Regular.

Trunk:

*Size.*—Average.

*Surface texture.*—Shaggy.

Branches:

*Size.*—Average.

*Surface texture.*—Shaggy.

*Color.*—A light dull brown; this color is not particularly distinctive of the subject variety, however.

*Lenticels — Numbers.*—Numerous.

*Lenticels — Size.*—Average.

LEAVES

Size:

*Generally.*—Medium to large as compared with other common plum cultivars.

Average length: Approximately 10.6 cm.

Average width: Approximately 4.9 cm.

Shape:

*Generally.*—Ovate.

Leaf tip:

*Shape.*—Acuminate.

Leaf base: Acute.

Leaf form: Acuminate, and occasionally lanceolate, acutely pointed.

Thickness:

*Generally.*—Thin.

Color:

*Upwardly disposed surfaces.*—Dark green, (Plate 24, J-4).

*Downwardly disposed surfaces.*—Pale green, (Plate 21, J-6).

Surface texture: Glabrous.

Marginal form: Finely serrate.

Petiole:

*Average length.*—Approximately 15.7 mm.

*Thickness.*—Approximately 1.6 mm.

Glands:

*Generally.*—Not readily evident.

FLOWER BUDS

Generally: Each bud develops into two flowers.

Form:

*Generally.*—Short, pointed, and free.

Size: Small and tender.

Pubescence: Not evident.

FLOWERS

Generally: The subject variety blooms at approximately the same time of the season as the Gar Fantasy Plum Tree (U.S. Plant Pat. No. 5,178).

Date of bloom: Considered average as compared with other common plum tree varieties.

Date of first bloom: In 1987, the first bloom was observed on February 28.

Date of full bloom: In 1987, full bloom was observed on March 8.

Size:

*Generally.*—Average.

Petals:

*Color.*—White. The petal color is not particularly distinctive of the subject variety, however.

FRUIT

Maturity when described: Ripe for harvesting and shipment approximately August 10 through August 15 under the ecological conditions currently prevailing in Fresno, Calif.

Size:

*Generally.*—Large as compared with the fruit produced by other common plum cultivars.

Uniformity: Uniform.

Average axial diameter: Approximately 58.9 mm.

Average diameter transverse and in the suture plane: Approximately 63.8 mm.

Average diameter transverse and at right angles with respect to the suture plane: Approximately 66.3 mm.

Form.

*Uniformity.*—Uniformly symmetrical.

Suture:

*Generally.*—The suture appears as an inconspicuous substantially shallow line which extends from the base but discontinues at the apex.

Ventral surface:

*Shape.*—Rounded slightly.

Lips:

*Size.*—Equal.

Stem cavity:

*Shape.*—Rounded and flaring.

*Depth.*—Approximately 6.4 mm.

*Breadth.*—Approximately 13.4 mm.

Base:

*Shape.*—Rounded.

Apex:

*Shape.*—Short and rounded, occasionally appearing slightly pointed. This particular feature may vary from fruit to fruit.

Pistil point:

*Position.*—Apical.

Skin:

*Thickness.*—Average, and tender.

Tenacious to flesh: Yes.

Tendency to crack: Not observed in the dry season.

Down:

*Quantity.*—Wanting.

Blush:

*Generally.*—The blush covers most of the fruit surface at commercial maturity, and makes the surface of the fruit appear pink, (Plate 6, L-8, Page 35). Further the pistil end of the fruit is more highly colored, (Plate 8, L-4, Page 39).

Flesh:

*Color.*—The flesh is a light pink color. The color is more intense near the skin and pit cavity, respectively, (Plate 5, G-3, Page 33).

Amygdalin: Moderate.

Juice production: Scant.

Texture: Firm, crisp, and meaty at full commercial maturity.

Fibers.

*Generally.*—Few, fine and tender.

Ripening: Uneven, the variety appears to ripen earliest at the apex.

Flavor:

*Generally.*—Mild and considered subacid.

Aroma: Wanting.

Eating quality: Good.

STONE

Attachment: The subject is most accurately characterized as a semi-freestone fruit although it may appear on first analysis as a freestone fruit. The stone typically will separate cleanly from the flesh.

Size:

*Generally.*—Average.

Average length: Approximately 20.2 mm.

Average breadth: Approximately 16 mm.

Average thickness: Approximately 9.1 mm.

Form:

*Generally.*—Oval, although occasionally ovate forms may be evident.

Hilum:

*Shape.*—Narrow and oval.

Apex:

*Shape.*—Acute, and occasionally acuminate.

Sides: Equal and flattened.

Surface texture: Irregularly furrowed, especially along the ventral edge. Further, the stone appears ridged and pitted throughout.

Ridges:

*Shape.*—Rounded.

Pits:

*Shape.*—Elongated.

Ventral edge:

*Thickness.*—Thin.

Dorsal edge:

*Shape.*—Narrow.

Ridges:

*Form.*—Continuous.

Color of stone: Salmon, (Plate 10, A-7, Page 43).

Use: The subject variety produces a fresh market-type plum.

Keeping quality: Good.

Resistance to insects and diseases: Average as compared with other common plum cultivars.

Although the new variety of plum tree possesses the described characteristics when grown under the ecological conditions prevailing in Fresno, Calif., in the central part of the San Joaquin Valley, it is to be understood that variations of the usual magnitude and characteristics incident to changes in growing conditions, fertilization, pruning and pest control are to be expected.

Having thus described and illustrated my new variety of plum tree, what is new and desired to be secured by Letters Patent is:

1. A new and distinct variety of plum tree, substantially as illustrated and described and which produces fruit which are somewhat remotely similar to the fruit borne by the Gar Fantasy Plum Tree (U.S. Plant Pat. No. 5,178) but which is distinguished therefrom and characterized principally as to novelty by bearing semi-freestone fruit which are ripe for commercial harvesting and shipment approximately August 10 through August 15 under the ecological conditions prevailing in Fresno, Calif., the subject variety producing fruit which have an attractive light red skin color, and a pink colored flesh.

* * * * *

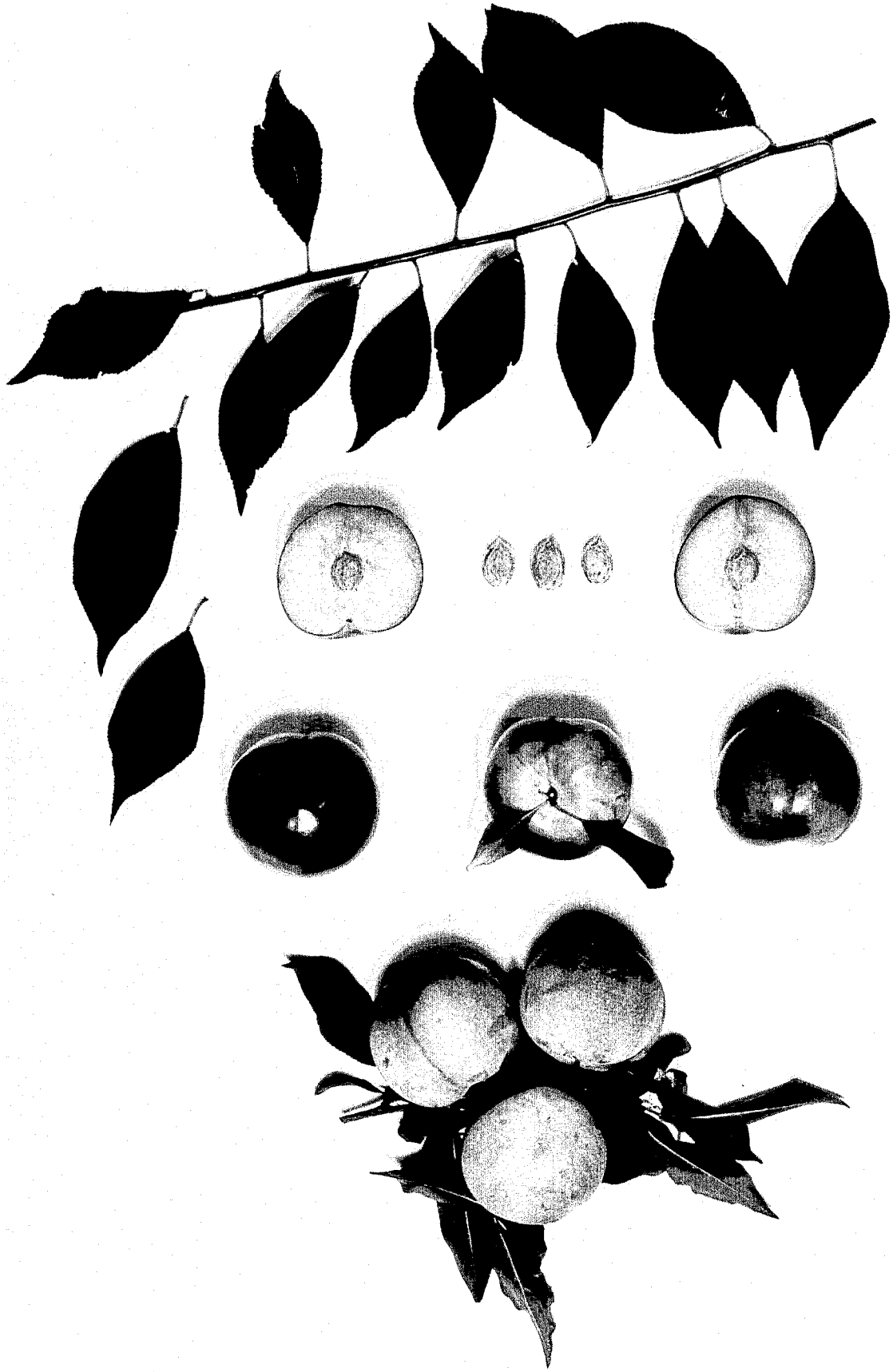

UNITED STATES PATENT AND TRADEMARK OFFICE

CERTIFICATE OF CORRECTION

PATENT NO. : PP. 7,076

DATED : Dec. 19, 1989

INVENTOR(S) : John M. Garabedian

It is certified that error appears in the above-identified patent and that said Letters Patent is hereby corrected as shown below:

Column 1, Line 15

Delete "the", and Insert ---and---

Signed and Sealed this

Eighteenth Day of December, 1990

*Attest:*

HARRY F. MANBECK, JR.

*Attesting Officer*

*Commissioner of Patents and Trademarks*